United States Patent
Sweeney et al.

(10) Patent No.: US 7,356,366 B2
(45) Date of Patent: Apr. 8, 2008

(54) DEVICE FOR MONITORING FLUID STATUS

(75) Inventors: Robert J. Sweeney, Woodbury, MN (US); Julio C. Spinelli, Shoreview, MN (US); Rodney W. Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 501 days.

(21) Appl. No.: 10/909,926

(22) Filed: Aug. 2, 2004

(65) Prior Publication Data

US 2006/0025661 A1    Feb. 2, 2006

(51) Int. Cl.
*A61B 5/00* (2006.01)

(52) U.S. Cl. .................. 600/345; 600/368; 600/547

(58) Field of Classification Search ............... 600/368, 600/547, 345
See application file for complete search history.

(56) References Cited

U.S. PATENT DOCUMENTS

| | | | |
|---|---|---|---|
| 4,469,593 A * | 9/1984 | Ishihara et al. ............ 210/96.2 |
| 4,901,725 A | 2/1990 | Nappholz et al. |
| 5,174,286 A | 12/1992 | Chirife |
| 5,179,946 A | 1/1993 | Weiss |
| 5,318,597 A | 6/1994 | Hauck et al. |
| 5,469,859 A | 11/1995 | Tsoglin et al. |
| 5,490,323 A | 2/1996 | Thacker et al. |
| 5,522,860 A | 6/1996 | Molin et al. |
| 5,642,734 A * | 7/1997 | Ruben et al. ............... 600/506 |
| 5,722,997 A | 3/1998 | Nedungadi et al. |
| 5,817,135 A | 10/1998 | Cooper et al. |
| 5,824,029 A | 10/1998 | Weijand et al. |
| 5,978,707 A | 11/1999 | Krig et al. |
| 6,044,294 A | 3/2000 | Mortazavi et al. |
| 6,058,934 A * | 5/2000 | Sullivan .................... 600/308 |
| 6,076,015 A | 6/2000 | Hartley et al. |
| 6,151,524 A | 11/2000 | Krig et al. |
| 6,161,042 A | 12/2000 | Hartley et al. |
| 6,292,689 B1 * | 9/2001 | Wallace et al. ............ 600/547 |
| 6,317,632 B1 | 11/2001 | Krig et al. |
| 6,463,326 B1 | 10/2002 | Hartley et al. |
| 6,574,506 B2 | 6/2003 | Kramer et al. |

(Continued)

FOREIGN PATENT DOCUMENTS

| | | |
|---|---|---|
| WO | WO-9943385 | 9/1999 |
| WO | WO-0074775 A1 | 12/2000 |
| WO | WO-03077759 A1 | 9/2003 |

OTHER PUBLICATIONS

"International Search Report and Written Opinion for Application No. PCT/US2005/027277, dated mailed Nov. 14, 2005", 13 pgs.

(Continued)

*Primary Examiner*—Robert L. Nasser, Jr.
*Assistant Examiner*—Karen E Toth
(74) *Attorney, Agent, or Firm*—Schwegman, Lundberg & Woessner, P.A.

(57) ABSTRACT

A technique for determining a patient's hematocrit by an electrical impedance measurement is described. An implantable device may be configured to utilize the technique in order to assess a cardiac patient's fluid status. In order to determine the hematocrit, the electrical impedance of the blood is measured and mapped by a mapping function to a corresponding hematocrit value.

18 Claims, 2 Drawing Sheets

U.S. PATENT DOCUMENTS

| | | | |
|---|---|---|---|
| 2002/0002389 | A1 | 1/2002 | Bradley et al. |
| 2002/0107552 | A1 | 8/2002 | Krig et al. |
| 2002/0123768 | A1 | 9/2002 | Gilkerson |
| 2002/0123769 | A1 | 9/2002 | Panken et al. |
| 2003/0069609 | A1 | 4/2003 | Thompson |
| 2003/0105499 | A1 | 6/2003 | Hartley et al. |
| 2003/0114889 | A1 | 6/2003 | Huvelle et al. |
| 2003/0212316 | A1* | 11/2003 | Leiden et al. ............... 600/323 |
| 2004/0049237 | A1 | 3/2004 | Larson et al. |
| 2004/0054268 | A1* | 3/2004 | Esenaliev et al. ........... 600/322 |
| 2004/0102908 | A1 | 5/2004 | Larson et al. |
| 2004/0116820 | A1 | 6/2004 | Daum et al. |

OTHER PUBLICATIONS

Cha, Kichul, et al., "An electronic method for rapid measurement of haematocrit in blood samples", *Physiological Measurement*, 15 (2), (1994), 129-137.

Freeberg, S., "Cross-Checking of Transthoracic Impedance and Acceleration Signals", U.S. Appl. No. 10/696,729, filed Oct. 29, 2003.

Kim, J., et al., "Cardiac Cycle Synchronized Sampling of Impedance Signal", U.S. Appl. No. 10/612,388, filed Jul. 2, 2003.

Krig, David B., "Apparatus and Method for Treating Ventricular Tachyarrhythmias", U.S. Appl. No. 11/073,818, filed Mar. 7, 2005, 61 pgs.

Larson, Dennis E., et al., "Minute Ventilation Sensor With Automatic High Pass Filter Adjustment", U.S. Appl. No. 10/306,889, filed Nov. 27, 2002, 33 pages.

Maasrani, M., et al., "Continuous Measurements by Impedance of Haematocrit and Plasma Volume Variations During Dialysis", *Medical & Biological Engineering & Computing*, 35 (3), (May 1997), 167-171.

Pop, G. A., et al., "Catheter-based Impedance Measurements in the Right Atrium for continuuously monitoring Hematocrit and Estimating blood Viscosity Changes; an in vivo Feasibility Study in Swine", *Biosensors and Bioelectronics*, 19 (12), (Jul. 15, 2004), 1685-1693.

Stahmann, J. E., et al., "Implantable Devices and Methods Using Frequency-Domain Analysis of Thoracic Signal", U.S. Appl. No. 10/612,387, filed Jul. 2, 2003.

Zhang, Y., et al., "Methods and Apparatuses for Arrhythmia Detection and Classification Using Wireless ECG", U.S. Appl. No. 10/975,166, filed Oct. 28, 2004, 69 Pages.

* cited by examiner

DEVICE FOR MONITORING FLUID STATUS

FIELD OF THE INVENTION

This invention pertains to methods and apparatus for medical monitoring.

BACKGROUND

Cardiac failure refers to a condition in which the heart fails to pump enough blood to satisfy the needs of the body. It is usually due to some damage to the heart itself, such as from a myocardial infarction or heart attack. When heart failure occurs acutely, autonomic circulatory reflexes are activated that both increase the contractility of the heart and constrict the vasculature as the body tries to defend against the drop in blood pressure. Venous constriction, along with the reduction in the heart's ability to pump blood out of the venous and pulmonary systems (so-called backward failure), causes an increase in the diastolic filling pressure of the ventricles. This increase in preload (i.e., the degree to which the ventricles are stretched by the volume of blood in the ventricles at the end of diastole) causes an increase in stroke volume during systole, a phenomena known as the Frank-Starling principle. If the heart failure is not too severe, this compensation is enough to sustain the patient at a reduced activity level. When moderate heart failure persists, other compensatory mechanisms come into play that characterize the chronic stage of heart failure. The most important of these is the depressing effect of a low cardiac output on renal function. The increased fluid retention by the kidneys then results in an increased blood volume and further increased venous return to the heart. A state of compensated heart failure results when the factors that cause increased diastolic filling pressure are able to maintain cardiac output at a normal level even while the pumping ability of the heart is compromised.

Compensated heart failure, however, is a precarious state. If cardiac function worsens or increased cardiac output is required due to increased activity or illness, the compensation may not be able to maintain cardiac output at a level sufficient to maintain normal renal function. Fluid then continues to be retained, causing the progressive peripheral and pulmonary edema that characterizes overt congestive heart failure. Diastolic filling pressure becomes further elevated which causes the heart to become so dilated and edematous that its pumping function deteriorates even more. This condition, in which the heart failure continues to worsen, is decompensated heart failure. It can be detected clinically, principally from the resulting pulmonary congestion and dyspnea, and all clinicians know that it can lead to rapid death unless appropriate therapy is instituted. It would be advantageous if there were a convenient means by which the fluid status of a patient could be monitored in order to detect the physiologic changes leading to decompensated heart failure at an early stage before clinical symptoms become apparent.

DETAILED DESCRIPTION

Figure 1:
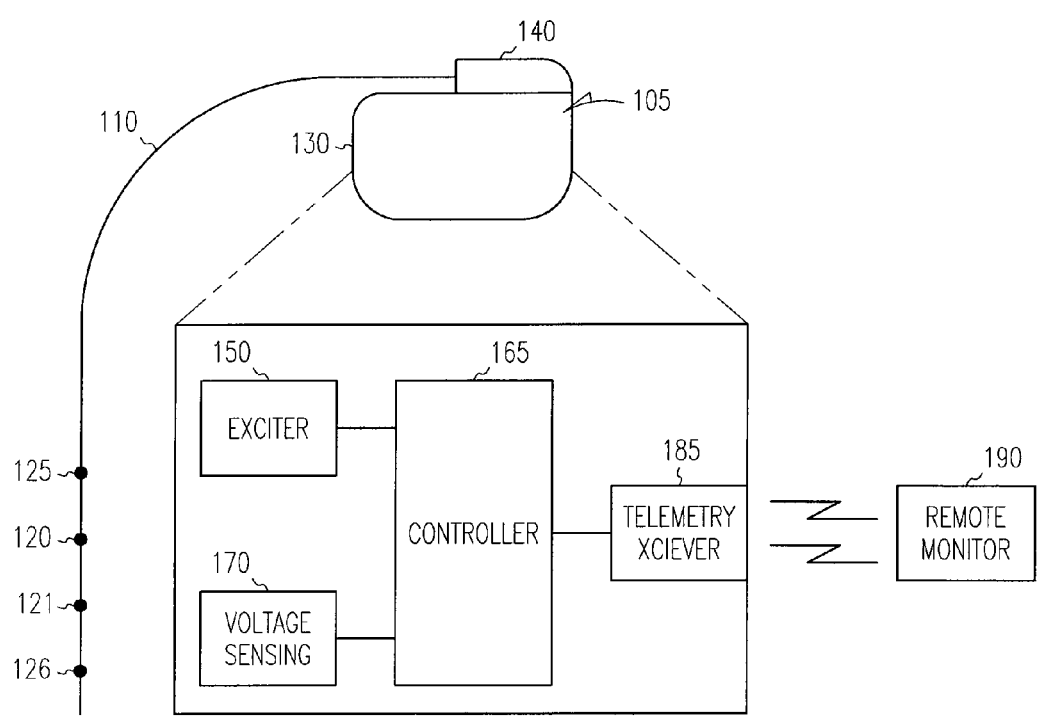
FIG. 1 illustrates an exemplary implantable device.

Decompensated heart failure is primarily a result of the heart failing to pump sufficient blood for the kidneys to function adequately and maintain fluid balance. When cardiac output falls, renal perfusion decreases which results in reduced glomerular filtration and reduced urine output. The decreased blood flow to the kidneys also activates the rennin-angiotensin system which further reduces renal perfusion and promotes the reabsorption of water and salt from the renal tubules. In the latter stages of this process, angiotensin stimulates secretion of aldosterone which causes a further increase in the reabsorption of sodium. The increase in sodium reabsorption raises the osmolarity of the blood which then elicits secretion of vasopressin and increased tubular reabsorption of water. Excess fluid retention brought about by renal compensation for heart failure has a diluting effect on the blood. Thus, one indication of deterioration in a heart failure patient's fluid status is a decrease in the patient's hematocrit, where the hematocrit is defined as the percentage of red blood cells in the blood. Described herein is an implantable device for monitoring a patient's fluid status by determining the concentration of cellular material in the blood from an electrical measurement.

The blood consists mainly of red blood cells suspended in non-cellular plasma, where the plasma is a solution of proteins and electrolytes, principally sodium and chloride. The blood is therefore a volume conductor which can be characterized electrically by its conductivity and permittivity. The conductivity and permittivity (or dielectric constant) of the medium determine the current density and polarization, respectively, which result if a known electric field is impressed in the medium. If charge is injected into the blood, the blood presents an impedance to the injected current which is a function of its conductivity and permittivity. A signal proportional to this impedance may be produced by impressing a known current field in a volume of blood surrounding two points and then measuring the voltage difference between the points. The measured voltage difference will then vary proportionately with changes in blood impedance. Since cellular material is a poorer conductor than an electrolyte solution, the impedance of the blood varies with the hematocrit so that as the concentration of red blood cells decreases, the impedance decreases. A measurement of the electrical impedance of the blood is therefore reflective of the hematocrit. Different embodiments of this technique are described below after a description of an exemplary implantable device.

1. Exemplary Implantable Device

The technique for monitoring fluid status as described herein may be implemented in an implantable device configured to perform monitoring only or in a cardiac rhythm management device configured to also deliver cardiac therapies such as bradycardia pacing, cardioversion/defibrillation therapy, or cardiac resynchronization therapy. The latter may be particularly useful since heart failure patients who need fluid status monitoring may also benefit from resynchronization pacing which improves cardiac function by causing the ventricles to contract in more coordinated manner. Examples of such devices are described in U.S. Pat. No. 6,574,506 and U.S. patent application Ser. No. 10/195,135, assigned to Cardiac Pacemakers, Inc., and hereby incorporated by reference in their entirety.

Implantable cardiac rhythm management devices such as pacemakers and cardioverter/defibrillators are battery-powered devices which are usually implanted subcutaneously on the patient's chest and connected to electrodes by leads threaded through the vessels of the upper venous system into the heart. FIG. 1 illustrates an implantable device 105 and a multi-conductor lead 110 having electrodes incorporated therein for performing the electrical measurements needed to assess fluid status. Device 105 may be, for example, a pacemaker capable of delivering bradycardia and/or anti-tachycardia pacing, an implantable cardioverter/defibrillator, a combination pacemaker/defibrillator, a drug delivery device, or a fluid status monitoring-only device. The device may therefore have one or more other leads with electrodes for disposition in the right atrium or ventricle or in a cardiac vein for sensing cardiac activity and/or delivering electrical stimulation to the heart. The lead 110 is adapted to be intra-vascularly disposed such as in an accessible location of the venous system or within a heart chamber. The device 105 includes a hermetically sealed housing 130, formed from a conductive metal, such as titanium. Housing 130 (also referred to as a "case" or "can") may be substantially covered over its entire surface by a suitable insulator, such as silicone rubber, except for at a window that forms a third electrode, referred to as a "case" or "can" electrode. A header 140, which may be formed of an insulating material, is mounted on housing 130 for receiving leads such as lead 110 or other leads used for cardiac sensing or stimulation. Contained within the housing 130 is the electronic circuitry for providing fluid status monitoring functionality to the device as described herein. In the case of a pacemaker or cardioverter/defibrillator, the housing would also contain circuitry for sensing and stimulating the heart.

As shown in FIG. 1, the device 105 includes a controller 165 which may be made up of discrete circuit elements but is preferably a processing element such as a microprocessor together with associated memory for program and data storage. The controller is programmed to perform the algorithms for monitoring fluid status which are described below. Interfaced to the controller 165 is an exciter 150 for delivering excitation current between excitation current electrodes 125 and 126 which are incorporated into the lead 110. The exciter 150 delivers the excitation current in accordance with parameters dictated by the controller which may include the current frequency, current amplitude, and the type of current waveform (e.g., square-wave, sinusoidal). In an example embodiment, the exciter includes a voltage controlled constant current source which is driven by a voltage signal $V_E$ to produce an excitation current waveform $I_E$. Also incorporated into the lead 110 are voltage sense electrodes 120 and 121 which are situated between the excitation current electrodes and connected to voltage sensing circuitry 170. Voltage sensing circuitry 170 is interfaced to the controller and includes amplification, filtering, and analog-to-digital conversion circuitry for processing the voltage difference signal produced by the electrodes 120 and 121.

Also interfaced to the controller 165 is a telemetry transceiver 185 capable of communicating with an external programmer or remote monitoring device 190. An external programmer wirelessly communicates with the device 105 and enables a clinician to receive data and modify the programming of the controller. The remote monitoring device 190 similarly communicates with the device 105 and is further interfaced to a patient management network (e.g., via an internet connection) which allows clinical personnel at remote locations to receive data from the device.

2. Estimation of Hematocrit from Impedance Measurement

As noted above, the electrical impedance of the blood varies with the hematocrit. A signal proportional to the impedance of the blood may be produced by impressing a current field from a constant current source between two electrodes immersed in the blood and then measuring the voltage difference therebetween. In the device illustrated in FIG. 1, the exciter delivers a predetermined amount of current between excitation current electrodes 125 and 126 of lead 110 with voltage sense electrodes 120 and 121 located between the excitation current electrodes 125 and 126. (Other embodiments may utilize electrodes incorporated into different leads or may use the can as an electrode.) The voltage difference measured between the voltage sense electrodes 120 and 121 is thus proportional to the electrical impedance of the blood. A particular measured voltage difference $V_m$ may be mapped to an estimated hematocrit value $Hct_{est}$ by a mapping function F:

$$Hct_{est}=F(V_m)$$

The mapping function F relates particular values of the voltage measurement to corresponding hematocrit values and, in general, will depend upon the particular current field produced by the excitation electrodes, the physical locations of the voltage sense electrodes, and the volume of blood in which the voltage sense electrodes are immersed. The mapping function may therefore by empirically determined under actual or simulated conditions and expressed as either a continuous or discrete function, the latter being implemented, for example, as a look-up table. (As will be described below, such an empirically determined mapping function may also be constructed to map other measured or derived parameters to an estimated hematocrit value.) Also, the physical configuration of the voltage sense and excitation current electrodes can be made so as to minimize changes in the voltage measurement signal $V_m$ due to changes in the impedance of the tissues other than blood surrounding the electrodes. If the voltage sense electrodes are spaced apart closely enough, the impedance between them will be almost completely due to the volume of blood surrounding the electrodes. Similarly, if the excitation current electrodes closely straddle the voltage sense electrodes, the current field produced by them will not vary appreciably with changes in the impedance of the surrounding tissues.

Figure 2:
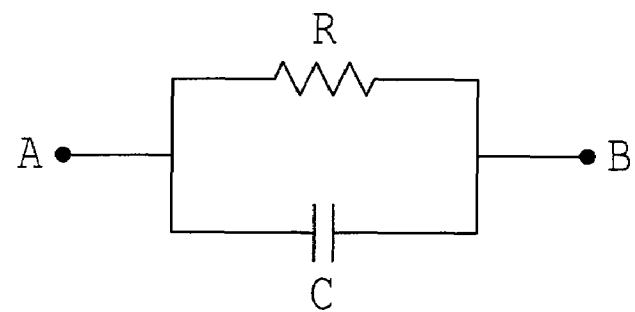
FIG. 2 is a circuit model of the blood impedance.

FIG. 2 shows two arbitrary points labeled A and B in a volume of blood. The impedance to a current flow between the two points can be modeled as an equivalent resistance R proportional to the blood's conductivity in parallel with an equivalent capacitance C proportional to the blood's permittivity. The impedance Z between the two points A and B in the blood is thus:

$$Z=R/(1+j\omega CR)$$

where $\omega$ is the frequency of the applied excitation current. Other models of the blood impedance could also be used such as a resistance representing plasma conductivity in parallel with reistance in series with a capacitance representing both the conductivity and permittivity of the red blood cells. The analysis is similar, however, to that set forth below.

Whatever the physical positions of points A and B in FIG. 2 and the value of Z, the voltage measurement signal $V_m$ derived as the potential difference between the voltage sense electrodes will vary proportionately with any changes in Z which occur due to changes in the blood's conductivity and/or permittivity. The voltage measurement signal can therefore be regarded as a virtual impedance measurement $Z_m$. (The impedance $Z_m$ would be the impedance between two points in a volume of blood which a spaced apart at a distance such that an injected current of unit amplitude between the points produces a voltage difference equal to $V_{m'}$). The virtual impedance $Z_m$ is made up of a resistive component $R_m$ and a reactive or capacitive component $1/\omega C_m$:

$$Z_m = R_m/(1+j\omega C_m R_m)$$

Increasing the concentration of red blood cells in the blood increases $R_m$ because cellular material is a poorer conductor than the solution of electrolytes which make up the plasma. The red blood cells also permit separations of charges to exist and therefore constitute a distributed capacitance (i.e., permittivity) which increases as the concentration of red blood cells increases.

Although both $R_m$ and $C_m$ increase as the concentration of red blood cells increases, the capacitive component of the impedance is small relative to the resistive component so that the overall impedance increases with increasing hematocrit. Except at very high excitation current frequencies, therefore, an increased hematocrit produces an increase in the magnitude of $Z_m$, where the magnitude of $Z_m$ is defined as:

$$|Z_m| = R_m/(1+\omega^2(C_m R_m)^2)^{1/2}$$

In one embodiment, the mapping function F is constructed in order to map the magnitude of the blood impedance to an estimated hematocrit value. The amplitude of the voltage measurement signal $V_m$, designated as $|V_m|$, is equal to $|Z_m|$ and may be mapped to a hematocrit value by a mapping function $F_Z$:

$$Hct_{est} = F_Z(|Z_m|)$$

Since the magnitude of the blood impedance $|Z|$ is dependent upon the excitation current frequency, the mapping function $F_Z$ is either defined only at a selected excitation current frequency or is made frequency dependent. In the latter case, the mapping function $F_Z$ takes into account the fact that the reactive portion of the impedance $Z_m$ increases with increasing excitation current frequency which tends to decrease the total impedance.

As noted above, the capacitance $C_m$ is due almost entirely to the presence of red blood cells in the blood. In another embodiment, a mapping function $F_C$ is constructed which maps values of the capacitance of the blood $C_m$ to a hematocrit value:

$$Hct_{est} = F_C(C_m)$$

Figure 3:
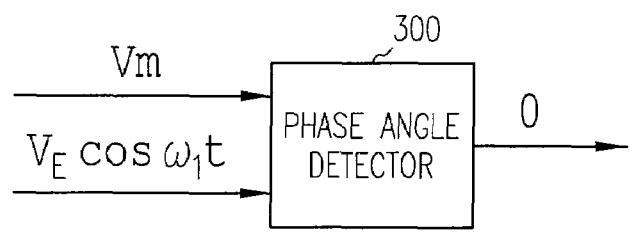
FIG. 3 illustrates a phase angle detector for processing the voltage difference signal.

The value of $C_m$ may be derived from measurements of the voltage difference $V_m$. When the excitation current is applied at DC or at relatively low frequencies, $V_m$ reflects only the resistive portion of the impedance so that $V_m$ is then equal to $R_m$. Once $R_m$ is found in this manner, $C_m$ may be derived by detecting the phase angle between the excitation current waveform and the voltage measurement signal waveform at an excitation current frequency $\omega_1$ where the capacitive component of the impedance $Z_m$ is evident. FIG. 3 illustrates this technique where the voltage measurement signal $V_m$ and a signal $V_E \cos \omega_1 t$ used to drive the exciter 150 and which is in phase with the excitation current are input to a phase angle detector 300. The phase angle detector may either be implemented as discrete hardware or as code executed by the controller. The output of the phase angle detector is a phase angle $\Phi_1$ which may be used to derive $C_m$ as follows:

$$C_m = R_m / \omega_1 \tan \Phi_1$$

Alternatively, the magnitude of $Z_m$ may be measured at the excitation current frequency of $\omega_1$ with the value of $C_m$ then being calculated from the impedance formula as:

$$C_m = ((R_m/|Z_m|)^2 - 1)^{1/2})/\omega_1 R_m$$

where the magnitude $|Z_m|$ is measured as the amplitude of $V_m$ at the excitation current frequency of $\omega_1$.

In addition to being a function of hematocrit, the blood impedance $Z_m$ also depends upon the electrolyte concentration in the blood. The electrolytes in the blood are made up primarily of sodium and chloride with smaller amounts of other salts and charged proteins. The concentration of these electrolytes in the plasma may vary in an individual patient which would then affect the measured impedance of the blood. In order to take this into account, a mapping function may be constructed which maps both a measured impedance $Z_m$ (e.g., the amplitude of the voltage difference signal $V_m$) and a measured electrolyte concentration E to an estimated hematocrit value:

$$Hct_{est} = F_{Z,E}(Z_m, E)$$

Figure 4:
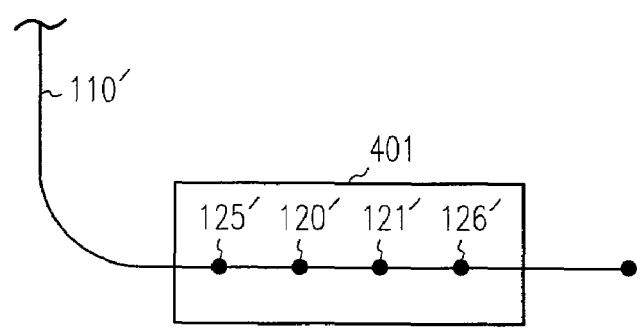
FIG. 4 shows a modified lead for determining plasma impedance.

In order to determine the electrolyte concentration E for use with the $F_{Z,E}$ mapping function, the resistivity of the blood plasma $R_P$ is determined using voltage sense electrodes which are immersed in a sample of the patient's plasma. FIG. 4 illustrates a modified lead 110' which may be used for this purpose where the voltage sense electrodes 120' and 121' are surrounded by a sleeve 401 made of a material (e.g., Goretex) which is impermeable to blood cells but permeable to the constituents of blood plasma. The excitation current electrodes 125' and 126' may also be enclosed within the sleeve 401. The electrodes 120', 121', 125', and 126' are connected to the device 105 in manner similar to that of their unprimed counterparts illustrated in FIG. 1. An impedance measurement between the voltage sense electrodes 120' and 121' is performed as described above to derive a plasma resistivity value $R_p$ which can then be mapped to an estimated electrolyte concentration E by an empirically determined mapping function $F_E$:

$$E = F_E(R_p)$$

The estimated electrolyte concentration is then used in conjunction with the impedance measurement of whole blood to estimate the hematocrit using the $F_{Z,E}$ mapping function as described above. In another modification, a temperature sensor may be included in an intravascular lead and employed by the implantable device to measure the temperature of the blood, which temperature measurement may then be incorporated into the mapping function for mapping an impedance measurement to an estimated hematocrit value.

The estimated hematocrit value $Hct_{est}$ may be calculated by the device at programmed intervals or upon receiving a command from an external device such as an external programmer. In the former case, changes in fluid status as determined by the hematocrit may be trended over time and stored for later analysis by a clinician. The estimated hematocrit may also be compared with a specified limit range so that an alarm flag is set internally by the device if the hematocrit is above or below the limit range, indicating fluid loss or fluid retention, respectively. Setting the alarm flag may also result in the implantable device transmitting an alarm message to a remote monitoring device which may be further communicated to clinical personnel over a patient management network.

Besides being used to estimate hematocrit, the measurement of blood impedance may also be used to adjust other impedance sensing modalities which an implantable device may possess. For example, an implantable device may utilize impedance measurements to calculate minute ventilation or cardiac stroke volume. Such calculations may be modified to take into account the impedance of the blood measured as described above.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A device, comprising:
    an exciter for outputting an excitation current waveform and impressing a current field between a pair of excitation current electrodes;
    voltage sensing circuitry for sensing a voltage difference signal between a pair of voltage sense electrodes disposed in a patient's blood and in the current field; and,
    a controller interfaced to the voltage sensing circuitry which is programmed to estimate the patient's hematocrit from the voltage difference signal with a mapping function that maps a capacitance value derived from the voltage difference signal to a hematocrit value.

2. The device of claim 1 further comprising a lead which incorporates the excitation current electrodes and the voltage sense electrodes, wherein the voltage sense electrodes are located between the excitation current electrodes.

3. The device of claim 1 wherein the controller is programmed to estimate the patient's hematocrit with a mapping function which maps the amplitude of the voltage difference signal to a hematocrit value.

4. The device of claim 1 wherein the controller is programmed to derive a capacitance value from the voltage difference signal by deriving a resistance value from the voltage difference signal at a first excitation frequency and measuring a phase angle between the excitation current waveform and the voltage difference signal at a second excitation frequency.

5. The device of claim 1 wherein the controller is programmed to derive a capacitance value from the voltage difference signal by deriving a resistance value from the voltage difference signal at a first excitation frequency and measuring the amplitude of the voltage difference signal at a second excitation frequency.

6. The device of claim 1 further comprising means for measuring a resistivity of the patient's plasma and wherein the controller is programmed to estimate the patient's hematocrit with a mapping function which maps the amplitude of the voltage difference signal and the resistivity of the patient's plasma to a hematocrit value.

7. The device of claim 1 wherein the controller is programmed to periodically estimate the patient's hematocrit which is stored and trended over time.

8. The device of claim 1 wherein the controller is programmed to compare the estimated hematocrit value with a specified limit range and set an alarm flag if the estimated hematocrit value is out of the specified limit range.

9. The device of claim 8 wherein the controller is programmed to transmit an alarm message to a remote monitoring device if the alarm flag is set.

10. A method for monitoring the fluid status of a patient, comprising:
    outputting an excitation current waveform and impressing a current field between a pair of excitation current electrodes;
    sensing a voltage difference signal between a pair of voltage sense electrodes disposed in the patient's blood and in the current field; and,
    estimating the patient's hematocrit from the voltage difference signal with a mapping function that maps a capacitance value derived from the voltage difference signal to a hematocrit value.

11. The method of claim 10 wherein the voltage sense electrodes are located between the excitation current electrodes in a single lead.

12. The method of claim 10 further comprising estimating the patient's hematocrit with a mapping function which maps the amplitude of the voltage difference signal to a hematocrit value.

13. The method of claim 11 further comprising deriving a capacitance value from the voltage difference signal by deriving a resistance value from the voltage difference signal at a first excitation frequency and measuring a phase angle between the excitation current waveform and the voltage difference signal at a second excitation frequency.

14. The method of claim 11 further comprising deriving a capacitance value from the voltage difference signal by deriving a resistance value from the voltage difference signal at a first excitation frequency and measuring the amplitude of the voltage difference signal at a second excitation frequency.

15. The method of claim 10 further comprising measuring a resistivity of the patient's plasma and estimating the patient's hematocrit with a mapping function which maps the amplitude of the voltage difference signal and the resistivity of the patient's plasma to a hematocrit value.

16. The method of claim 10 further comprising periodically estimating the patient's hematocrit and trending the estimated hematocrit values over time.

17. The method of claim 10 further comprising comparing the estimated hematocrit value with a specified limit range and setting an alarm flag if the estimated hematocrit value is out of the specified limit range.

18. The method of claim 17 further comprising transmitting an alarm message to a remote monitoring device if the alarm flag is set.

* * * * *

UNITED STATES PATENT AND TRADEMARK OFFICE
CERTIFICATE OF CORRECTION

| | | |
|---|---|---|
| PATENT NO. | : 7,356,366 B2 | Page 1 of 1 |
| APPLICATION NO. | : 10/909926 | |
| DATED | : April 8, 2008 | |
| INVENTOR(S) | : Sweeney et al. | |

It is certified that error appears in the above-identified patent and that said Letters Patent is hereby corrected as shown below:

In column 8, line 28, in Claim 13, delete "claim 11" and insert -- claim 10 --, therefor.

In column 8, line 34, in Claim 14, delete "claim 11" and insert -- claim 10 --, therefor.

Signed and Sealed this

Fifth Day of August, 2008

JON W. DUDAS
*Director of the United States Patent and Trademark Office*